(12) United States Patent
Burstein

(10) Patent No.: US 8,658,185 B2
(45) Date of Patent: Feb. 25, 2014

(54) KIT USEFUL FOR TREATING TUMORS AND LESIONS OF THE SKIN AND THE MUCOUS MEMBRANES

(75) Inventor: Pinchas Burstein, Ramat Hasharon (IL)

(73) Assignee: Innovative Pharmaceutical Concepts (IPC) Inc., Tortola (VG)

( * ) Notice: Subject to any disclaimer, the term of this patent is extended or adjusted under 35 U.S.C. 154(b) by 141 days.

(21) Appl. No.: 12/350,039

(22) Filed: Jan. 7, 2009

(65) Prior Publication Data

US 2009/0123568 A1 May 14, 2009

Related U.S. Application Data

(60) Division of application No. 10/490,213, filed as application No. PCT/IL02/00804 on Oct. 2, 2002, now abandoned, which is a continuation-in-part of application No. 09/968,771, filed on Oct. 3, 2001, now Pat. No. 7,128,903.

(51) Int. Cl.
*A61K 8/02* (2006.01)

(52) U.S. Cl.
USPC ........................................... 424/401

(58) Field of Classification Search
USPC ........................................... 424/401
See application file for complete search history.

(56) References Cited

U.S. PATENT DOCUMENTS

| | | | |
|---|---|---|---|
| 3,924,623 A | 12/1975 | Avery | |
| 4,195,095 A | 3/1980 | Sheffner | |
| 4,588,590 A | 5/1986 | Bernstein | |
| 4,595,591 A | 6/1986 | Mardi et al. | |
| 5,166,176 A | 11/1992 | Obagi et al. | |
| 5,276,032 A | 1/1994 | King et al. | |
| 5,322,856 A | 6/1994 | Martin | |
| 5,547,988 A | 8/1996 | Yu et al. | |
| 5,573,786 A | 11/1996 | Grabo et al. | |
| 5,654,336 A | 8/1997 | Yu et al. | |
| 5,700,656 A | 12/1997 | Liu | |
| 5,791,801 A | 8/1998 | Miller | |
| 5,874,463 A | 2/1999 | Ancira | |
| 6,235,474 B1 | 5/2001 | Feinberg | |
| 6,281,203 B1 | 8/2001 | Touzan et al. | |
| 6,284,281 B1 | 9/2001 | Chevalier et al. | |
| 6,391,860 B1 | 5/2002 | McGrath | |
| 6,503,946 B1 | 1/2003 | Agholme | |
| 6,573,043 B1 | 6/2003 | Cohen et al. | |
| 7,128,903 B2 | 10/2006 | Burstein | |
| 2003/0087960 A1 | 5/2003 | Burstein | |

FOREIGN PATENT DOCUMENTS

| | | |
|---|---|---|
| EP | 0048443 A1 | 9/1981 |
| EP | 1450771 | 9/2004 |

(Continued)

OTHER PUBLICATIONS

Krajian et al, Histopathological Technic, 2nd Edition, The C. V. Mosby Company (St. Louis, 1952), pp. 17-25, 123-133.

(Continued)

*Primary Examiner* — Benjamin Packard

(57) ABSTRACT

The pharmaceutical preparation useful for treating a skin or mucous membrane lesion is provided. The pharmaceutical preparation including, as active ingredients, a therapeutically effective amount of trichloroacetic acid and hydrochloric acid, or trichloroacetic acid and formic acid or all three of these acids and optionally a crosslinking/fixating/preserving agent. Additional preparations are also described.

2 Claims, 20 Drawing Sheets

(56) References Cited

FOREIGN PATENT DOCUMENTS

| | | | |
|---|---|---|---|
| JP | 8208407 | | 8/1996 |
| WO | 9639119 | A1 | 12/1996 |
| WO | 9817247 | A1 | 4/1998 |
| WO | 0045808 | A1 | 8/2000 |
| WO | 0071105 | A2 | 11/2000 |
| WO | 0105387 | A2 | 1/2001 |
| WO | 02102363 | A1 | 12/2002 |

OTHER PUBLICATIONS

"Remove", Webster's Online Dictionary, www.merriam-webster.com, Dec. 12, 2007.

XP-002318874, Derwent English Language abstract of CN1059228C, Dec. 6, 2000; Accession No. 2001-123819[14].

XP-002318873, Derwent English Language abstract of CN1273827, Nov. 22, 2000; Accession No. 2001-183741[19].

International Preliminary Examination Report Dated Jul. 15, 2003 From the International Preliminary Examining Authority Re.: Application No. PCT/IL02/00804.

Fig. 30 b1
Fig. 30 b2
Fig. 30 a1
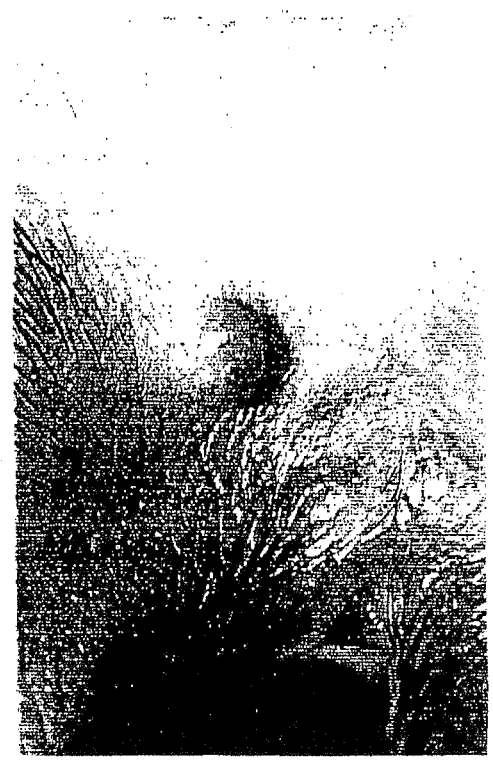
Fig. 30 a2

Fig. 31 a1
Fig. 31 b1
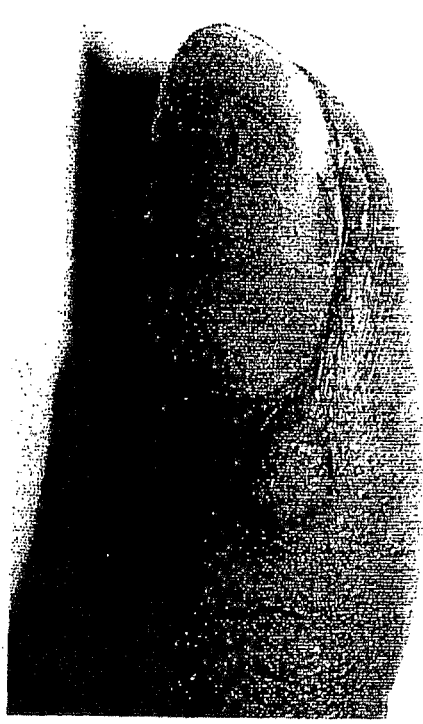
Fig. 31 a2
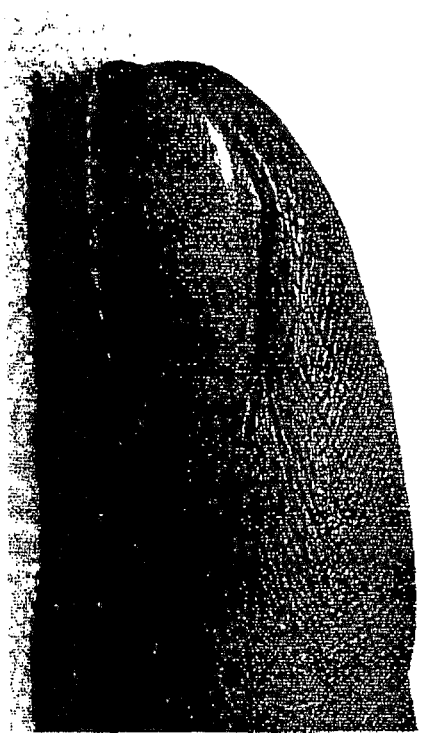
Fig. 31 b2

Fig. 32 b1
Fig. 32 b2
Fig. 32 a1
Fig. 32 a2

Fig. 33 b1
Fig. 33 b2
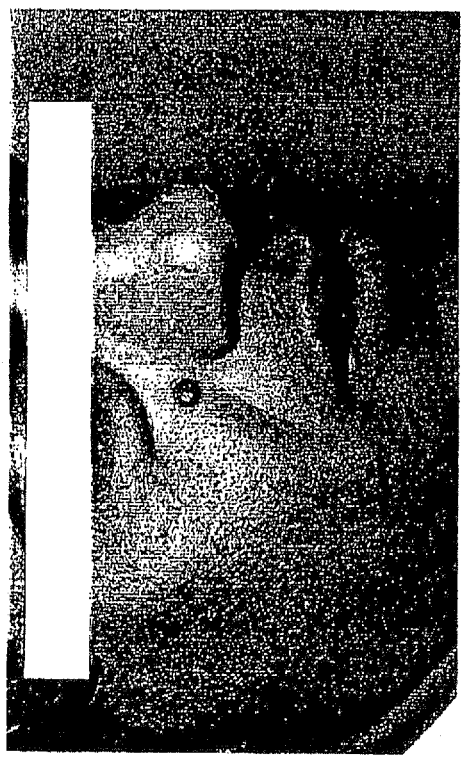
Fig. 33 a1
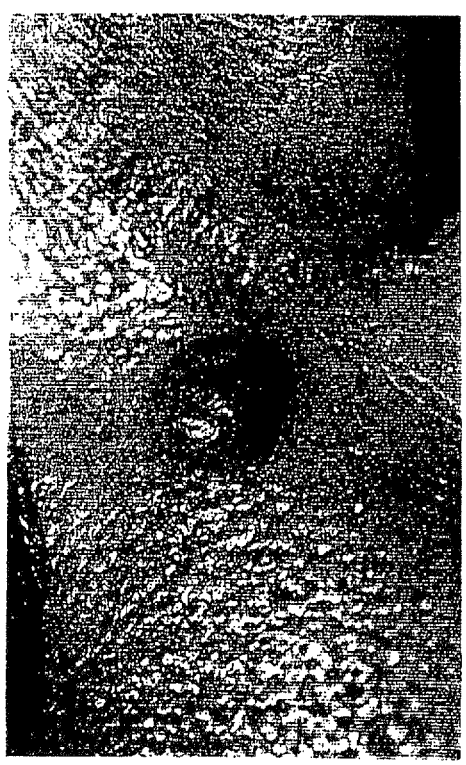
Fig. 33 a2

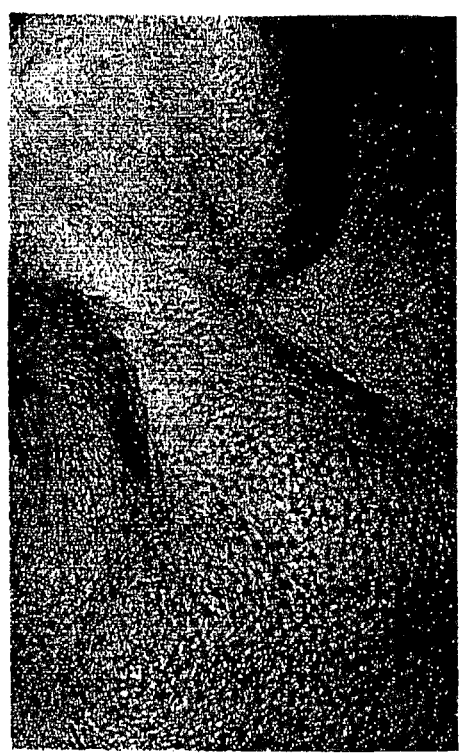
Fig. 33 c1
Fig. 33 c2

Fig. 36 a1
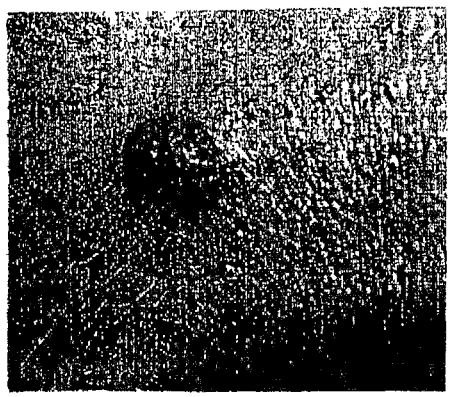
Fig. 36 a2
Fig. 36 a3
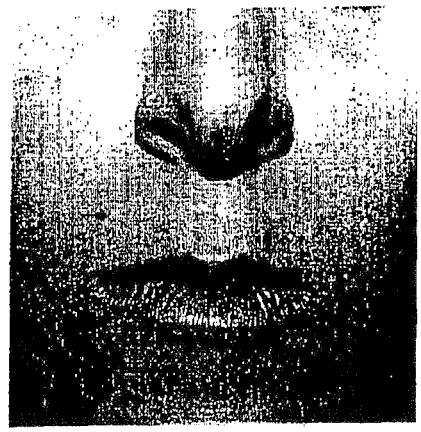
Fig. 36 b

Fig. 37 b
Fig. 37 a1
Fig. 37 a2

Fig. 38 b1
Fig. 38 b2
Fig. 38 a1
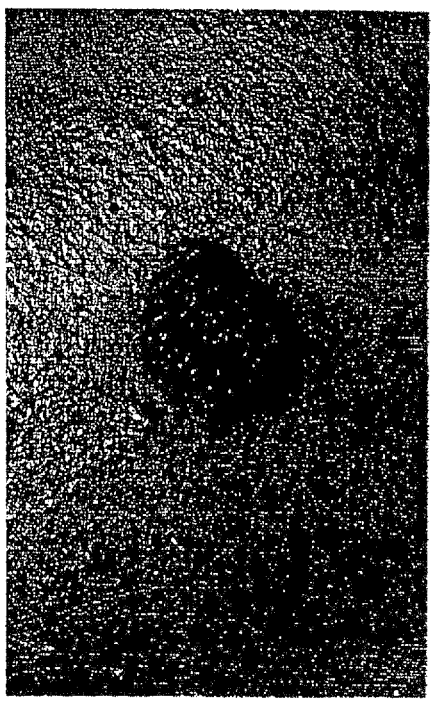
Fig. 38 a2

Fig. 38 c1
Fig. 38 c2

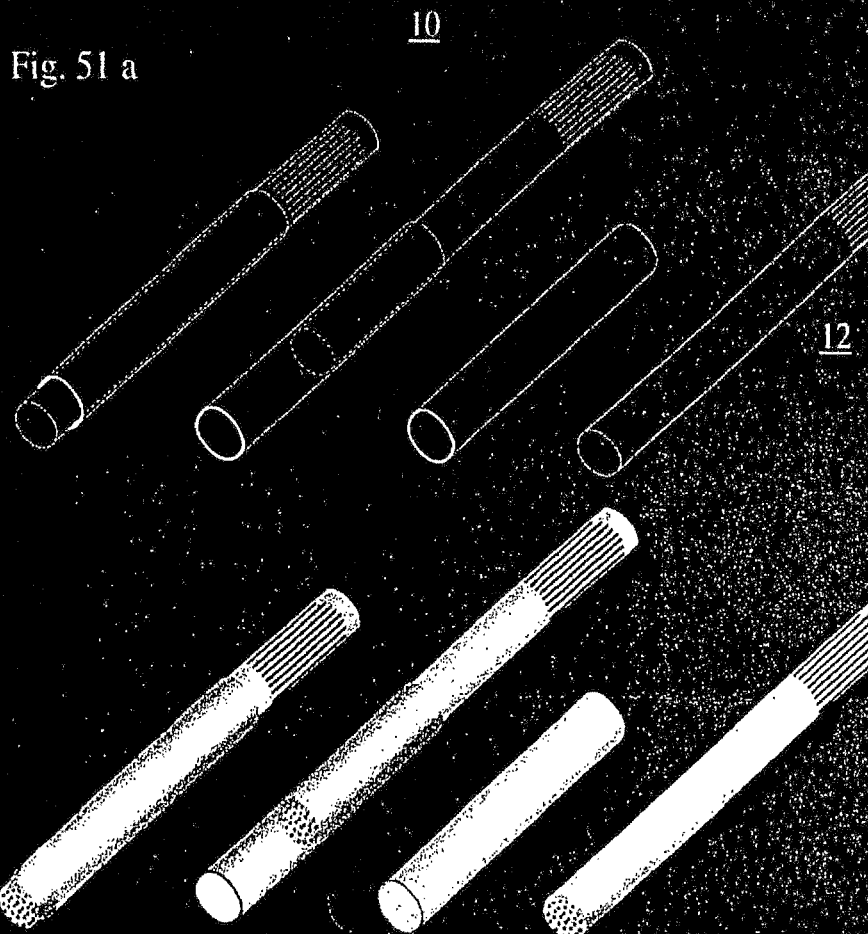
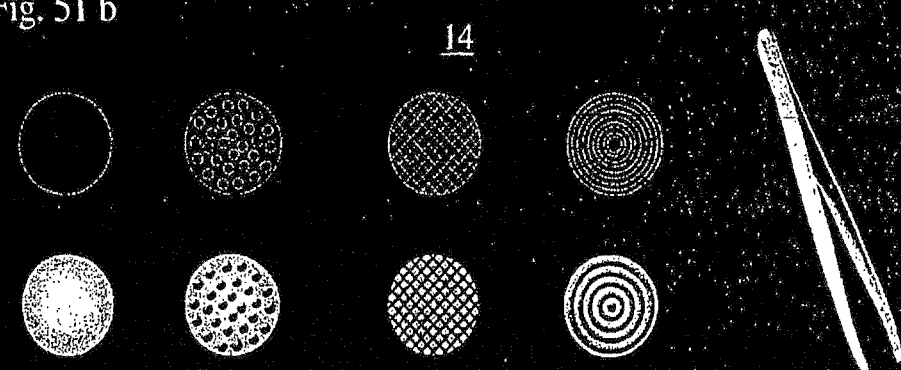

KIT USEFUL FOR TREATING TUMORS AND LESIONS OF THE SKIN AND THE MUCOUS MEMBRANES

CROSS-REFERENCE TO RELATED APPLICATIONS

The present application is a divisional of application Ser. No. 10/490,213, filed Mar. 31, 2004, with is a continuation-in-part of application Ser. No. 09/968,771, filed Oct. 3, 2001. The entire content of both applications is incorporated herein by reference.

FIELD AND BACKGROUND OF THE INVENTION

The present invention relates to pharmaceutical preparations useful in the treatment of tumors and lesions of the skin and the mucous membranes, and methods and kits using same.

Human skin and mucousal membranes support a wide range of growth abnormalities which exhibit a wide range of sizes, shapes and colors. Although not always dangerous to the individual, such growth abnormalities are frequently cosmetically unappealing and as such are oftentimes a cause of great discomfort. In addition, such growth abnormalities are also prone to injury and infection and can be a source of physical pain or discomfort.

Genital warts (condylomata acuminata) are a sexually transmitted disease caused by the human papilloma virus (HPV). Since the 1970's it has been increasingly clear that infections by the same virus are closely implicated in the aetiology of anogenital squamous cell carcinomas and in their precursors known as dysplasia, intraepithelial neoplasia (CIN) or squamous intraepithelial lesions (SIL).

Cutaneous melanoma, another skin lesion, which is also known as "the great masquerader", is often recognized by its dark color, although some tumors, defined as amelanotic melanomas, have little or no pigmentation and as such are hard to detect and diagnose.

Due to limited diagnostic capabilities, physicians often rely upon biopsy specimen analysis for accurate diagnosis of a suspected malignant melanoma.

However, at present, most lesions which are not suspected as being malignant are not biopsied but are rather treated via methods such as cryosurgery, laser therapy or electrocauterization which destroy the treated skin region making histopathological diagnosis impossible.

In addition, such treatment methods oftentimes lead to complications," including pain, bleeding and discharge as well as infections, blistering and hematomas. Such complications often necessitate the application of localized antibiotics as well as bandaging and as such are liable to cause further discomfort to the individual treated.

Furthermore, with such treatments, the healing process is liable to be slow and prolonged inevitably concluding with the formation of an ugly scar which can be a source of discomfort, particularly when appearing on exposed areas of the body such as the neck and face.

Finally, such methods are also limited by the use of expensive equipment not available in most clinics; furthermore, cryosurgery requires a current and permanent supply of liquid nitrogen, and is thus limited by the logistic hardships imposed by such requirements.

An alternative method of treating lesions such as, warts and condylomata acuminata, involves topical application of Solcoderm" (manufactured and distributed by Solco Basel AG, Switzerland), a medication which includes nitric acid and nitrous acid or metal nitrite.

Adequate results using Solcoderm" are achieved only if the recommended storage temperature and the use-by dates indicated are observed as accurately as possible, since fluctuations in the nitrite concentration due to storage temperature, storage time or prolonged exposure to oxygen may severely decrease the effectiveness of Solcoderm™.

In addition, it has been observed that preparations such as Solcoderm™, when inactive, present an increased danger of side effects and may for example lead to ulcerations on healthy skin.

Furthermore, due to the use of nitric acid, which is a strong oxidizing acid, Solcoderm™ treatment tends to destroy lesion tissue to an extent substantially negating the possibility of accurate post treatment histopathological study and diagnosis.

U.S. Pat. No. 5,573,786 describes an improved composition of Solcoderm™ which overcomes the stability limitations described above. This composition includes nitric acid and nitrite reduction products formed by reacting aqueous nitric acid with a primary C1-$C_s$ alkanol. The primary alkanol is converted to C1-Cs alkanoic acid and carbon dioxide, with the simultaneous formation of nitrate reduction products.

As stated in U.S. Pat. No. 5,573,786 this improved composition is useful for the treatment of common and plantar warts, pedal mycosis and onychomycosis.

Topical treatment methods using Solcoderm" or its derivatives are oftentimes preferred over laser therapy or cryotherapy, since such treatment methods cause less of a discomfort to the treated individual and are easier and less expensive to conduct. However, the currently available composition is indicated for the treatment of warts and condylomata only.

Although a study performed by Cesarini from the Department of Dermatology, Foundation Rothschild, Paris, France (Dermatologica 168; suppl. 1. pp. 15-25 (1984>>) suggested that the fixative properties of Solcoderm™ are adequate for histopathological diagnosis of post-treatment scabs, the same study demonstrated that when H & E staining is used (the single histochemical staining method used), the cellular elements stain in pale pink while the extra cellular compartment does not stain at all; furthermore, anisocytosis, anisokariosis and polychromatophilia, the usual landmarks of cytologists, cannot be observed and described.

There is thus a widely recognized need for, and it would be highly advantageous to have, compositions and methods of using same for effectively treating skin or mucous membrane lesions while enabling post treatment histopathological analysis of treated tissue.

SUMMARY OF THE INVENTION

According to one aspect of the present invention there is provided a pharmaceutical preparation useful for treating a skin or mucous membrane lesion comprising, as active ingredients, therapeutically effective amounts of at least two active ingredients selected from the group consisting of trichloroacetic acid, hydrochloric acid and formic acid. According to another aspect of the present invention there is provided a pharmaceutical preparation useful for treating a skin or mucous membrane lesion comprising, as active ingredients, therapeutically effective amounts of at least two said active ingredients selected from the group consisting of trichloroacetic acid, hydrochloric acid and formic acid and a crosslinking/fixating/preserving agent.

According to further features in preferred embodiments of the invention described below, there is provided an ampoule containing the pharmaceutical preparation described herein.

According to an additional aspect of the present invention there is provided an article-of-manufacturing comprising packaging material and a pharmaceutical preparation being identified for treatment of skin or mucous membrane lesions, the pharmaceutical preparation including, as active ingredients, therapeutically effective amounts of trichloroacetic acid and hydrochloric acid, or trichloroacetic acid and formic acid, or hydrochloric acid and formic acid, or all three acids.

According to still an additional aspect of the present invention there is provided a method of treating a skin or mucous membrane lesion, the method comprising: (a) applying to the skin or mucous membrane lesion a pharmaceutical preparation including, as active ingredients, therapeutically effective amounts of at least two active ingredients selected from the group consisting of trichloroacetic acid, hydrochloric acid and formic acid.

According to still further features in the described preferred embodiments the method further comprising repeating step (a) at predetermined time intervals.

According to still further features in the described preferred embodiments, a concentration of the trichloroacetic acid, the hydrochloric acid and the formic acid is selected such that application of the preparation to the skin or mucous membrane lesion leads to drying and separation of the skin or mucous membrane lesion from a base tissue thereof.

According to still further features in the described preferred embodiments a concentration of the trichloroacetic acid, the hydrochloric acid and the formic acid is selected such that application of the pharmaceutical preparation to the skin or mucous membrane lesion preserves a morphology of tissue thereof thereby enabling histopathological analysis of the tissue.

According to still further features in the described preferred embodiments a concentration of the trichloroacetic acid is selected from a range of 5%-97% (w/w), the concentration of the hydrochloric acid is selected from a range of 3%-38% (w/w) and the concentration of the formic acid is selected from a range of 0.1%-85% (w/w), preferably about 3%.

According to still further features in the described preferred embodiments the pharmaceutical preparation further comprising at least one crosslinking/fixating/preserving agent selected from the group consisting of formaldehyde; paraformaldehyde; glutaraldehyde; glyoxal; carbodi-imide; a formaldehyde donor; sodium hydroxymethyl glycinate; diazolidinyl urea; imidazolidinyl urea; dimethylol-5,5-dimethylhydantoin; dimethylol urea; 2-bromo-2-nitropropane 1,3-diol; quaternium-15; parabens; 5-chloro-2 methylisothiazolin-3-one; 1,2-dibromo-2,4-dicyanobutane; ethanol and other alcohols; polyol.

According to still further features in the described preferred embodiments the pharmaceutical preparation further comprises at least one agent selected from the group consisting of cytotoxic drugs, anti acne drugs, corticosteroids, anti-inflammatory agents, antibiotics, anti-viral agents, anti-psoriactic agents, keratinolytic agents, skin penetration enhancers, local anaesthetic agents, antiseptic agents, metal ions, tars and urea.

According to yet an additional aspect of the present invention there is provided an article-of-manufacturing comprising packaging material and a pharmaceutical preparation being identified for treatment of skin or mucous membrane lesions, the pharmaceutical preparation including, as active ingredients, about 48% (w/w) trichoroacetic acid, about 8% (w/w) hydrochloric acid and about 3% (w/w) formic acid.

As used herein throughout, the term "about" refers to ±10%.

According to still further features in the described preferred embodiments the pharmaceutical preparation includes about 48% (w/w) trichloroacetic acid, about 8% (w/w) hydrochloric acid, about 3% (w/w) formic acid and about 4% (w/w) formaldehyde.

According to a further aspect of the present invention there is provided a method of treating and biopsying a skin or mucous membrane lesion, the method comprising: (a) applying to the skin or mucous membrane lesion at least one mummifying preparation, so as to obtain, following a mummification period, a mummified skin or mucous membrane lesion; and (b) collecting the mummified skin or mucous membrane lesion.

According to still further features in the described preferred embodiments the mummifying preparation includes, as active ingredients, therapeutically effective amounts of at least two agents selected from the group consisting of trichloroacetic acid, hydrochloric acid and formic acid.

According to still further features in the described preferred embodiments a concentration of the trichloroacetic acid is selected from a range of 5%-97% (w/w), the concentration of the hydrochloric acid is selected from a range of 3%-38% (w/w) and the concentration of the formic acid is selected from a range of 0.1%-85% (w/w).

According to still further features in the described preferred embodiments the mummifying preparation further comprises a crosslinking/fixating/preserving agent.

According to still further features in the described preferred embodiments the mummifying preparation includes, as active ingredients, about 48% (w/w) trichloroacetic acid, about 8% (w/w) hydrochloric acid and about 3% (w/w) formic acid.

According to still further features in the described preferred embodiments the pharmaceutical preparation further comprises about 4% (w/w) formaldehyde.

According to still further features in the described preferred embodiments the method further comprising staining the mummified skin or mucous membrane lesion prior to histopathological examination. According to still a further aspect of the present invention there is provided a kit useful for treating a skin or mucous membrane lesion comprising: (a) an applicator including a reservoir configured for storing a pharmaceutical preparation, the reservoir being capped at one end by a removable applicator tip; (b) a mechanism for forcing a pharmaceutical preparation stored by the reservoir through the applicator tip; and (c) a plurality of applicator tips, each being sized and configured for applying the pharmaceutical preparation stored by the reservoir to a specific type, shape or size of a skin or mucous membrane lesion.

According to still further features in the described preferred embodiments the kit further comprising at least one ampoule containing a pharmaceutical preparation including, as active ingredients, therapeutically effective amounts of at least two active ingredients selected from the group consisting of trichloroacetic acid, hydrochloric acid and formic acid.

According to still a further aspect of the present invention there is provided an adhesive bandage useful for treating skin lesions comprising: (a) an applicator pad containing a pharmaceutical preparation including at least two active ingredients selected from the group consisting of trichloroacetic acid, hydrochloric acid and formic acid; and (b) an adhesive tape attached to the applicator pad, the adhesive tape being configured for attaching to a skin region so as to position the applicator pad against a portion of the skin region including a skin lesion thereby applying the pharmaceutical preparation to the skin lesion.

According to still further features in the described preferred embodiments the pharmaceutical preparation including, as active ingredients, therapeutically effective amounts of at least two active ingredients selected from the group consisting of trichloroacetic acid, hydrochloric acid and formic acid.

According to still further features in the described preferred embodiments a concentration of the trichloroacetic acid is selected from a range of 5%-97% (w/w), the concentration of the hydrochloric acid is selected from a range of 3%-38% (w/w) and the concentration of the formic acid is selected from a range of 0.1%-85% (w/w).

According to still further features in the described preferred embodiments the pharmaceutical preparation includes, as active ingredients, about 48% (w/w) trichloroacetic acid, about 8% (w/w) hydrochloric acid and about 3% (w/w) formic acid.

According to still further features in the described preferred embodiments the pharmaceutical preparation further comprises about 4% (w/w) formaldehyde.

According to still a further aspect of the present invention there is provided a pharmaceutical preparation useful for treating a skin or mucous membrane lesion comprising, as active ingredients, therapeutically effective amounts of at least two agents selected from the group consisting of trichloroacetic acid, hydrochloric acid, formic acid, monochloroacetic acid, dichloroacetic acid, glycolic acid, citric acid, kojic acid, acetic acid, azelaic acid, phosphoric acid, thioglycolic acid, salicylic acid and their salts and phenol.

According to yet a further aspect of the present invention there is provided a pharmaceutical preparation useful for treating a skin or mucous membrane lesion comprising, as active ingredients, therapeutically effective amounts of at least one agent selected from the group consisting of trichloroacetic acid, hydrochloric acid, formic acid, monochloroacetic acid, dichloroacetic acid, glycolic acid, citric acid, kojic acid, acetic acid, azelaic acid, phosphoric acid, thioglycolic acid, salicylic acid and their salts and phenol and at least one crosslinking/fixating/preserving agent.

According to still further features in the described preferred embodiments the at least one crosslinking/fixating/preserving agent is selected from the group consisting of formaldehyde; paraformaldehyde; glutaraldehyde; glyoxal; carbodi-imide; a formaldehyde donor; sodium hydroxymethyl glycinate; diazolidinyl urea; imidazolidinyl urea; dimethylol-5,5-dimethylhydantoin; dimethylol urea; 2-bromo-2-nitropropane 1,3-diol; quaternium-15; parabens; 5-chloro-2 methylisothiazolin-3-one; 1,2-dibromo-2,4-dicyanobutane; ethanol and other alcohols; polyol.

According to still a further aspect of the present invention, there is provided a pharmaceutical preparation useful for treating a skin or mucous membrane lesion, comprising as active ingredients, therapeutically effective amounts of at least one agent selected from the group consisting of trichloroacetic acid, hydrochloric acid, formic acid, monochloroacetic acid, glycolic acid, acetic acid, azelaic acid, phosphoric acid, thioglycolic acid, salicylic acid and their salts and phenol, and at least one nonoxidizing organic or inorganic acid.

According to yet a further aspect of the present invention, there is provided a pharmaceutical preparation useful for treating a skin or mucous membrane lesion, comprising, as active ingredients, at least one nonoxidizing organic or inorganic acid and at least one crosslinking/fixating/preserving agent selected from the group consisting of formaldehyde; paraformaldehyde; glutaraldehyde; glyoxal; carbodi-imide; a formaldehyde donor; sodium hydroxymethyl glycinate; diazolidinyl urea; imidazolidinyl urea; dimethylol-5,5-dimethylhydantoin; dimethylol urea; 2-bromo-2-nitropropane 1,3-diol; quaternium-15; parabens; 5-chloro-2 methylisothiazolin-3-one; 1,2-dibromo-2,4-dicyanobutane; ethanol and other alcohols; polyol.

The present invention successfully addresses the shortcomings of the presently known configurations by providing a pharmaceutical preparation useful for removing skin or mucous membrane lesions and for fixating tissues of skin or mucous membrane lesions thereby enabling both treatment and histopathological analysis of skin or mucous membrane lesions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 30a1-38c2 are images of patients treated with one embodiment of the pharmaceutical preparation of the present invention, (a1, a2)-prior to treatment, (b1, b2, c1 and c2) following treatment.

FIGS. 30a1-b2 Intradermal nevus; 1 topical treatment; scab dropped 20 days after treatment; pictures taken 27 days after treatment. FIGS. 31a1-b2-Veruca vulgaris; 3 topical treatments; complete healing after 50 days. FIGS. 32a1-b2 Intradermal nevus; 1 topical treatment; scab dropped 25 days after treatment; pictures taken 31 days after treatment. FIGS. 33a1-c2-Intradermal nevus; 1 topical treatment, scab dropped 22 days after treatment, pictures taken 36 (FIG. 33b1 and 2) and 65 (FIG. 33c1 and 2) days after treatment. FIGS. 36a1-b-Two intradermal nevi; 1 topical treatment; scabs dropped 16 & 18 days after treatment; pictures taken 22 days after treatment. FIGS. 37a1-b-Pigmented skin tags; 1 topical treatment; scabs dropped 9-14 days after treatment; pictures taken 30 days after treatment. FIGS. 38a-c-Seborrheic keratosis; 2 topical treatments, the second performed 32 days after the first one (FIG. 38b1 and 2); complete healing is observed 57 days following initial treatment (FIG. 38c1 and 2).

FIGS. 39-42 illustrates Hematoxylin & eosin staining. The specimens illustrate a skin fragment showing squamous epithelium with dermis (magnifications: ×40, ×100, ×200, ×400, respectively). The preservation of the tissue (if normal is given a score 4 out of 4) is not as optimal as routine formalin fixated tissue, shows some artifactual shrinkage, and would be given a grading score of 3 to 3.5 of 4. The architecture of epithelium and dermal tissues are sufficiently preserved. The specimens present the following: (a) normal lining keratinizing epithelium, (b) normal dermal adnexal structures, (c) clusters and nests of intradermal melanocytic cells showing no cellular atypia or pleomorphism. The diagnosis in these specimens is that of an intradermal nevus. Had a suspected malignancy been present in these specimens, the tissue preservation is sufficiently good to enable its identification. FIG. 43 illustrates Van-Gieson staining of the specimen of FIGS. 39-42. This stain highlights connective tissue (preferential to elastic and collagen fibers) with a red-pink uniform color. FIG. 44 illustrates Cytokeratin staining of the specimen of FIGS. 39-42. Cytokeratin stain, which is an immunohistochemical stain, stains the cell membranes of epithelial cells of both the epidermis and adnexal structures (hair follicles). The stain shows a "rim" of brown staining that is limited to the cell membrane with no staining of the cytoplasm or nucleus. In the skin, the stain is most prominent in the most basally situated epithelial cells, and thereby delineates the basement membrane of the skin. FIGS. 45-46 illustrates HMB 45 staining of the specimen of FIGS. 39-42. This stain is a selective immunohistochemical (membrane) stain for malignant melanocytes and does not stain the benign nevus cells in the specimen. FIGS. 47-50 illustrate AgNOR staining of the specimen of FIGS. 39-42. This stain is not limited to cell types, and as such stains both epithelial and stromal cells (e.g. squamous cells and smooth muscle cells). The staining does not delineate cell membranes but rather stains (in dark brown) the nuclei and para-nuclear cytoplasm in a non-uniform punctate pattern.

FIGS. 51a-b illustrate an applicator configured for applying the preparations of the present invention to skin or mucous membrane lesions.

DESCRIPTION OF THE PREFERRED EMBODIMENTS

Figure 1:
FIG. 1 is an image of a mouse skin section fixed with preparation A-Ia according to the present invention, and stained with H&E; magnification×100.

The present invention is of a pharmaceutical preparation which can be used to treat skin or mucous membrane lesions. Specifically, the present invention can be used to remove skin or mucous membrane lesions in a manner which enables histopathological examination of removed lesion tissue.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

As used herein, the phrase "skin or mucous membrane lesions" generally refers to benign or malignant pathologies of skin or mucousal membrane tissues. Examples of skin or mucous membrane lesions treatable by the preparations and methods of the present invention include, but are not limited to, dermatoses, seborrheic keratosis, intradermal nevus, verucae, condylomata acufninata, seborrheic dermatitis, atopic dermatitis, eczema, hyperkeratosis, acne (acne vulgaris), psoriasis; bacterial, fungal and/or viral infections of the skin and/or the mucous membranes/tissues, diabetic and/or ischemic wounds/ulcers, decubitus ulcers and oral lesions (lesions of the oral mucosa) such as aphthous stomatisis.

According to one aspect of the present invention there is provided a pharmaceutical preparation useful for treating a skin or mucous membrane lesion. The pharmaceutical preparation comprises, as active ingredients, therapeutically effective amounts of at least one, preferably at least two, active ingredients selected from the following: trichloroacetic acid, hydrochloric acid, formic acid, monochloroacetic acid, dichloroacetic acid, glycolic acid, citric acid, kojic acid, acetic acid, azelaic acid, phosphoric acid, thioglycolic acid, salicylic acid and their salts and phenol. Preferably, the pharmaceutical preparation includes trichloroacetic acid, hydrochloric acid and optionally formic acid.

The pharmaceutical preparation may also advantageously include a crosslinking/fixating/preserving agent, examples of which are given hereinbelow.

Table 1 below lists possible combinations and concentrations of 15 presently preferred active ingredients suitable for use as the pharmaceutical preparation of the present invention.

TABLE 1

Presently preferred active ingredient combinations

| | Hydrochloric acid | trichloroacetic acid | Formic acid | Formaldehyde |
|---|---|---|---|---|
| Preparation 1 (A-Ib)* | 8% | 48% | 3% | — |
| Preparation 2 (A-Ia)* | 10% | 33% | 4% | — |
| Preparation 3 | 13% | 20% | 5% | — |
| Preparation 4 | 8% | 48% | — | — |
| Preparation 5 | 10% | 33% | — | — |
| Preparation 6 | 13% | 20% | — | — |
| Preparation 7 (A-Ib+)* | 8% | 48% | 3% | 4% |
| Preparation 8 (A-Ia+)* | 10% | 33% | 4% | 4% |
| Preparation 9 | 13% | 20% | 5% | 4% |
| Preparation 10 | — | 46% | 5% | — |
| Preparation 11 | — | 46% | 5% | 4% | final concentrations of active ingredients given in weight per weight (w/w)
*designation used here in below for these specific preparations.

According to a preferred embodiment of the present invention, the concentration of each of the active ingredients is selected such that application of the preparation to the skin or mucous membrane lesion leads to drying (mummification) and separation of the skin or mucous membrane lesion from its base tissue.

As used herein, the term "mummification" and its derivatives include dehydration and/or fixation and/or preservation of tissue in such manner that following rehydration a mummified tissue is (i) rehydratable; and (ii) amenable to meaningful histopathological staining and analysis.

The phrase "meaningful histopathological staining" refers to a histopathological staining that allows clear identification between pathological and normal state. Examples of suitable stains used for obtaining histopathological staining are given in the Brief Description of the Drawings section above.

As has already been stated in the background section above, although a study performed by Cesarini from the Department of Dermatology, Foundation Rothschild, Paris, France (Dermatologica 168; suppl. 1. pp. 15-25 (1984)) suggested that the fixative properties of Solcoderm™ are adequate for histopathological diagnosis of post-treatment scabs, the same study demonstrated that when H & E staining is used (the single histochemical staining method used) the cellular elements stain in pale pink while the extra cellular compartment does not stain at all; furthermore, anisocytosis, anisokaryosis and polychromatophilia, the usual landmarks of cytologists, cannot be observed and described. These findings may be explained by the fact that prior art preparations such as Solcoderm™, utilize nitric acid, a strong oxidizing acid, which tends to destroy treated tissues.

Hence, the type and concentrations of the active ingredient(s) of the preparation of the present invention are preferably selected such that cellular and extracellular morphology of treated lesions is preserved following detachment of the lesion from its surrounding skin or membrane tissue.

Furthermore, the active ingredient(s) of the preparation of the present invention are also preferably selected so as to facilitate penetration of the pharmaceutical preparation into the treated tissue. This feature is particularly advantageous especially in cases where crosslinking agents are used, since such agents oftentimes exhibit poor tissue penetration properties. Hence, the active ingredients are preferably selected to synergize with the crosslinking agents with respect to dehydration and mummification.

As described in the Examples section below, lesions treated according to the teachings of the present invention, completely separated from their base tissue, and fell off, in some cases, a few days following a single topical application of the preparation of the present invention. It is important to note that since this separation does not occur until re-epithelialization ends, the skin exposed following separation of a lesion is dry, smooth, healthy, and manifests no signs of local infection, i.e., suppuration, bleeding or festering.

As is described in the Examples section which follows, the preparations of the present invention are also capable of preserving the morphology and composition of tissue and cells treated thereby. It stands to reason that these preservation capabilities of the present preparation underlie or contribute to its effectiveness in treating skin lesions, since tissue drying/mummification probably leads to separation of the skin lesion from the skin. Thus, when formulating additional pharmaceutical preparations useful for treating skin or mucous membrane lesions, consideration can also be given to tissue preservation qualities of preparation ingredients.

Due to these tissue preservation capabilities, treatment with the pharmaceutical preparation of the present invention enables meaningful post treatment analysis of the architectural and histological morphology of treated tissues, a feature which is extremely important especially in cases where lesion tissue cannot be accurately diagnosed prior to treatment, which feature is absent in prior art preparations. Example 1 below details morphology preservation qualities of the pharmaceutical preparation of the present invention and compares such qualities with those of a tissue preservative (i.e., formaldehyde) and Solcoderm™, a prior art pharmaceutical preparation.

To enhance such tissue preservation features, the pharmaceutical preparation of the present invention preferably includes at least one crosslinking/fixating/preserving agent, the concentration of which is selected according to the lesion tissue to be treated. Examples of suitable crosslinking/fixating/preserving agents include, but not limited to formaldehyde; paraformaldehyde; glutaraldehyde; glyoxal; carbodiimide; a formaldehyde donor; sodium hydroxymethyl glycinate; diazolidinyl urea; imidazolidinyl urea; dimethylol-5,5-dimethylhydantoin; dimethylol urea; 2-bromo-2-nitropropane 1,3-diol; quaternium-15; parabens; 5-chloro-2 methylisothiazolin-3-one; 1,2-dibromo-2,4-dicyanobutane; ethanol and other alcohols; and polyols.

The pharmaceutical preparation of the present invention may also include at least one agent which functions in improving penetration of the preparation into lesion tissue, preventing infections, preventing lesion cell proliferation and/or reducing discomfort associated with treatment.

Examples of agents falling into this category include, but are not limited to, cytotoxic drugs, anti acne drugs, corticosteroids, anti-inflammatory agents, antibiotics, anti-viral agents, anti-psoriatic agents, keratinolytic agents, skin penetration enhancers, local anaesthetic agents, antiseptic agents, metal ions, tars and urea.

According to another preferred embodiment of the present invention the pharmaceutical preparation includes about 48% (w/w) trichloroacetic acid, about 8% (w/w) hydrochloric acid and about 3% (w/w) formic acid. As is described in the Examples section below, such a formulation was extremely effective in treating various forms of skin lesions.

The pharmaceutical preparation of the present invention is preferably provided as an aqueous solution contained in, for example, an ampoule or any other suitable container.

The pharmaceutical preparation of the present invention can also be provided in a paste (ointment or cream), or gel form by mixing the active ingredient(s) of the pharmaceutical preparation of the present invention with suitable thickeners or gelating materials the likes of which are well known in the art. Alternatively, when possible, the pharmaceutical preparation can be provided in a rehydratable powder form, as a tincture.

It will be appreciated that in cases of reactive or unstable active ingredients, the preparation of the present invention can be provided in two or more separate ampoules or other kinds of containers which can be combined prior to use.

For example, when crosslinking/fixating/preserving agents are used in the pharmaceutical preparation of the present invention, such agents may be provided in a separate ampoule and combined with other active ingredients immediately prior to use.

Preferably, the preparation of the present invention is provided as part of an article-of-manufacturing which also includes packaging material identifying the pharmaceutical preparation of the present invention as useful for treatment and/or preservation of a skin or mucous membrane lesion.

As already mentioned hereinabove, the pharmaceutical preparation of the present invention can be utilized to treat a variety of skin and mucousal membrane lesions.

Such treatment is effected by applying the pharmaceutical preparation to the lesion (see, Example 2 for further detail) using a syringe, a swab or a specially adapted applicator. A presently preferred applicator is further described in Example 5 of the Examples section which follows.

In cases where collection of the lesion tissue (typically in lesions of skin tissue) is desired for histopathological examination, application of the pharmaceutical preparation is followed by bandaging such that the mummified skin lesion tissue is retained by the bandage following separation, thus allowing post-collection treatment (e.g., rehydration) and histopathological analysis of the lesion tissue.

Application of the pharmaceutical preparation of the present invention can also be effected via a specialized adhesive bandage. Such a bandage is also described in Example 5 of the Examples section.

An adhesive bandage applicator is especially advantageous in cases where histopathological examination is desired, since it can also serve to collect the lesion tissue following separation.

Thus, the present invention provides a pharmaceutical preparation and methods of using same for treating and/or mummifying lesion tissue.

As is further detailed in the Examples section which follows, the preparation of the present invention is effective at both treating and mummifying lesion tissue.

In addition, the preparation of the present invention is harmless for use, free of side effects, while treatment therewith is only slightly discomforting to the patient.

Finally, since complete treatment can oftentimes be effected using a single application, the preparation of the present invention provides an easy, rapid and inexpensive method of removing lesions while minimizing scar tissue, infections and any other problems usually associated with prior art methods of skin lesion removal.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

In histopathology, most tissues are fixed prior to microscopic examination. Since fixation oftentimes precedes various tissue preparation steps, such as, for example, tissue staining, it is essential that a fixative is selected according to the tissue type to be fixed, and purpose of fixation.

Tissue fixation is caused by a complex series of chemical events which depend on the fixation protocol used and tissue type fixed. It is important that tissue morphology and composition is maintained as much as possible during fixation steps, such that fixed tissue accurately represents the living state of the tissue prior to fixation.

Although most fixation protocols aim to preserve tissue morphology and composition, some substances, e.g. lipids, are always lost unless special precautions are taken.

Most fixation protocols preserve the microanatomy of the tissues well enough to allow fixed tissues to be used in, for example, histopathological diagnosis.

To preserve microanatomy, most fixation protocols employ reagents which form crosslinks between proteins, since such crosslinks ensure preservation of protein structures which dictate cellular morphology.

Protein crosslinking is typically mediated by aldehyde groups; reactions between fixative agents, such as formaldehyde, and amino acids, such as lysine, form crosslinks between protein molecules.

Formaldehyde, glyoxal and glutaraldehyde have long been used as crosslinking agents. In the case of formaldehyde, the crosslinking reaction can be reversed during the first 24 hours of reaction by simply saturating the reaction with excess water. With glutaraldehyde, on the other hand, the reaction is rapid and irreversible.

One of the important effects of fixation on proteins is the extent of denaturation. For most routine histopathology analysis such denaturation is of no consequence. However, in the case of immunofluorescence, immunohistochemistry and high resolution electron microscopy it is clearly of considerable importance.

In such cases, mild fixating conditions are used such that antigenic sites are not greatly altered or destroyed or that morphology of large molecules remains unchanged.

Depending on the protein, glutaraldehyde fixation can cause a loss of up to 30 percent of a-helix structures, while fixation with osmium tetraoxide or post-osmication of glutaraldehyde-fixed material can cause the complete denaturation of the protein.

Due to tissue heterogeneity, no single fixation protocol is ideal for all tissue components or types. As such, researchers often use mixtures of fixatives which are formulated such that a limitation of one fixative agent is compensated for by another fixative agent in the mixture. In some mixtures, the components may react together, such as the case with aldehydes and oxidizing agents. If such mixtures are used, then the active components must be mixed immediately before use, otherwise, the effective concentration of each agent will be decreased, possibly to levels that are no longer effective.

Histopathological staining, including the use of a basement membrane/collagen stain to emphasize the basic architecture of a tissue or a neoplasm, are currently used as preliminary tissue analysis methods oftentimes prior to use of more accurate immunohistochemical analysis methods. Several choices of stains, including PAS, silver (reticulin) stains, or a trichrome stain, which is a three dye stain used for selective demonstration of muscle, collagen fibers, fibrin and erythrocytes.

The use of immunohistochemical methods has vastly improved diagnosis of tumors of uncertain origin. By using monoclonal and polyclonal antibodies for identifying protein structures, immunohistochemical methods enable accurate differentiation between various tumor types and as such represent the most valuable tool at the disposal of a histopathology investigator.

Since keratins are present in all epithelial cells, they represent highly sensitive markers for malignant cells of epithelial origin (e.g., carcinomas). There are more than 20 different subtypes of human keratin proteins each distinguished by a specific molecular weight and/or isoelectric point. Specific monoclonal antibodies have been developed against many of these subtypes and immunohistochemical studies have shown that some carcinomas have characteristic keratin profiles.

Although keratin expression is characteristic of epithelial cells, nonepithelial neoplasms may in rare instances show aberrant expression of keratin. Such tumors include lymphomas (especially anaplastic large cell lymphoma), various sarcomas, gliomas, epithelioid vascular tumors, and melanomas.

Melanoma, oftentimes presents as a poorly differentiated malignant neoplasm. Traditionally, Fontana-Masson or other silver-based stains for melanin and for the ultrastructural detection of melanosomes have assisted in the diagnosis of melanomas.

Melanomas typically have very little or no cytoplasmic keratin but do stain with antivimentin, antibodies directed against the S-100 protein which is a fairly stable antigen that withstands formaldehyde fixation and paraffin embedding, and antibodies directed against melanosomes.

In melanoma analysis, anti-S-100 staining is typically effected along with additional histopathological or immunohistopathological staining since the S-100 also appears in benign nevus cells, Langerhans histiocytes, many sacromas (liposarcomas and chondrosacromas), neural tumors (schwanomas, neurofibromas, and granular cell tumors), and certain carcinomas, such as those derived from the salivary gland, breast, and lung.

The identity of S-100 positive neoplasm as a melanoma is typically confirmed by reaction with HMB45, an antibody which recognizes a melanoma-specific antigen by reacting with melanoma cells and junctional nevus cells, but not normal melanocytes or intradermal nevus cells.

The distribution of nucleolar acidic proteins selectively stained by silver has become an important parameter for the cytohistologic diagnosis of malignancy. The silver-stained (Ag) proteins are located in nucleolar components which contain ribosomal genes and represent the interphase counterpart of metaphase nucleolar organizer regions (NORs). These proteins are therefore called Ag-NOR proteins. It has been repeatedly demonstrated that malignant tumors can be easily distinguished from corresponding benign lesions on the basis of a greater quantity of nucleolar Ag-NOR proteins.

Although the argyrophil method for NORs, known as the AgNOR technique, identifies NOR-associated proteins rather than NORs themselves, it is still considered highly specific. Crocker and Skilbek (J Clin Pathol 40; 885889; 1987) have shown that melanocarcinomas can readily be distinguished from naevocellular naevi by using the AgNOR method. Thus, the simplicity and applicability of the AgNOR method makes it a potentially powerful histopathological tool.

Example 1

Fixative Properties of the Pharmaceutical Preparations of the Present Invention

A series of tissue fixating/staining experiments were conducted in order to examine the fixating capability of each of the components of the pharmaceutical preparations of the present invention. In order to uncover possible synergistic relationships, all possible combinations of these components were tested.

The information obtained from these experiments was cross referenced with data regarding the corrosive nature of these components, the level of burning or pain they cause upon skin contact, and their ability to penetrate deeply into the tissue and soften it during treatment.

Three main components were tested: trichloroacetic acid (TCA), hydrochloric acid (HCl) and Formic acid (FA). These three main components of the preparation were tested alone and in various combinations as detailed in Table 2 below. In addition, Solcoderm™ and its new version (U.S. Pat. No. 5,573,786) were also tested and used as controls.

Materials and Methods

Sections of mouse skin 8 mm in diameter were submerged into 1 ml of a test preparation in glass tubes sealed with a rubber stopper, and incubated for 24 hours. The treated sections of mouse skin were then recovered, dried on absorbent paper and laid upon Petrie dishes, lined with two layers of absorbent paper. The skin sections were flattened and loosely taped to the absorbent paper using strips of breathing micropore tape and dried at room temperature (RT) for 30 days. Following complete skin drying, the specimens were sent for routine processing prior to being stained with histochemical and immunohistochemical stains, as detailed below. Skin treated with buffered formaldehyde 4% served as a control. The scoring of fixation quality seen in the different staining methods was determined according to the following key:

Score 1: Only the keratin and hair structures remain.

Score 2: Keratin and hair structures preserved, and the "architecture" of the tissue is present. Cellular detail is not present.

Score 3: Keratin and hair structures preserved, "architecture" preserved and the dermal tissue shows cellular detail. If a foreign, malignant or abnormal infiltrate was present in the specimen, identification thereof is likely.

Score 4: All elements of epithelium as well as the dermal tissue are preserved. Fixation and staining at levels 3-4 enable identification and preliminary diagnosis of a space-occupying lesion or a suspicion of malignancy.

Results and Discussion

The results, as summarized in Table 2 below, indicate synergism among TCA HCl and FA as expressed in preservation of both the architecture and cellular detail of the tissue section.

Figure 2:
FIG. 2 is an image of a mouse skin section fixed with preparation A-Ia according to the present invention, and stained with H&E; magnification×200.
Figure 3:
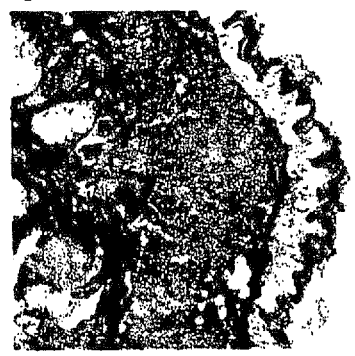
FIG. 3 is an image of a mouse skin section fixed with preparation A-Ia according to the present invention, and stained with H&E; magnification×400.
Figure 4:
FIG. 4 is an image of a mouse skin section fixed with preparation A-Ib according to the present invention, and stained with H&E; magnification×100.
Figure 5:
FIG. 5 is an image of a mouse skin section fixed with preparation A-Ib according to the present invention, and stained with H&E; magnification×200.
Figure 6:
FIG. 6 is an image of a mouse skin section fixed with Solcoderm™ and stained with H&E; magnification×100.
Figure 7:
FIG. 7 is an image of a mouse skin section fixed with Solcoderm™ and stained with H&E; magnification×400.
Figure 8:
FIG. 8 is an image of a mouse skin section fixed with buffered formaldehyde 4% and stained with H&E; magnification×100.
Figure 9:
FIG. 9 is an image of a mouse skin section fixed with buffered formaldehyde 4% and stained with H&E; magnification×200.
Figure 10:
FIG. 10 is an image of a mouse skin section fixed with preparation A-Ia according to the present invention, and stained with Van-Gieson; magnification×100.
Figure 11:
FIG. 11 is an image of a mouse skin section fixed with preparation A-Ia according to the present invention, and stained with Van-Gieson; magnification×200.
Figure 12:
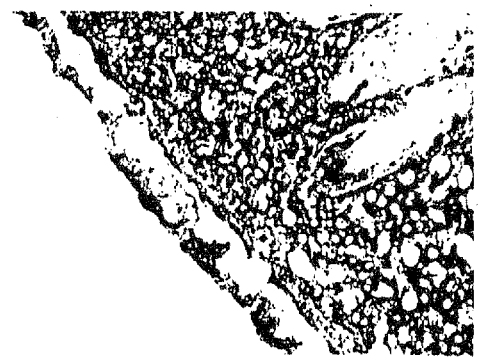
FIG. 12 is an image of a mouse skin section fixed with preparation A-Ia according to the present invention, and stained with Van-Gieson; magnification×400.
Figure 13:
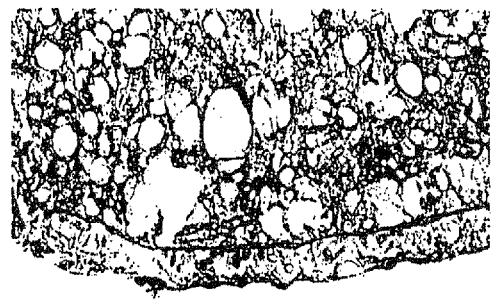
FIG. 13 is an image of a mouse skin section fixed with preparation A-Ia according to the present invention, and stained with Van-Gieson; magnification×400.
Figure 14:
FIG. 14 is an image of a mouse skin section fixed with Solcoderm™ and stained with Van-Gieson; magnification× 100.
Figure 15:
FIG. 15 is an image of a mouse skin section fixed with buffered formaldehyde 4% and stained with Van-Gieson; magnification×400.
Figure 16:
FIG. 16 is an image of a mouse skin section fixed with preparation A-Ib according to the present invention, and stained with Cytokeratin; magnification×200.
Figure 17:
FIG. 17 is an image of a mouse skin section fixed with Solcoderm™ and stained with Cytokeratin; magnification× 200.
Figure 18:
FIG. 18 is an image of a mouse skin section fixed with buffered formaldehyde 4% and stained with Cytokeratin; magnification×400.
Figure 19:
FIG. 19 is an image of a mouse skin section fixed with preparation A-Ia according to the present invention, and stained with AgNOR; magnification×200.
Figure 20:
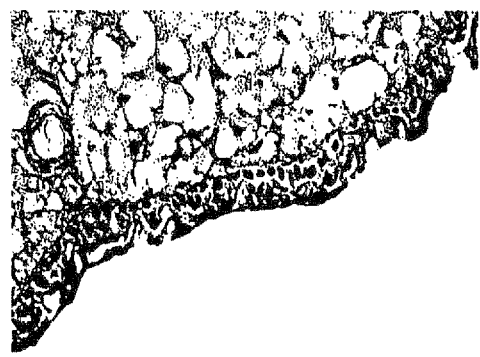
FIG. 20 is an image of a mouse skin section fixed with preparation A-Ia according to the present invention, and stained with AgNOR; magnification×400.
Figure 21:
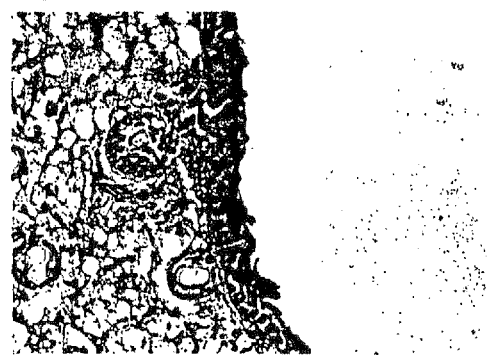
FIG. 21 is an image of a mouse skin section fixed with preparation A-Ia according to the present invention, and stained with AgNOR; magnification×400.
Figure 22:
FIG. 22 is an image of a mouse skin section fixed with preparation A-Ia according to the present invention, and stained with AgNOR; magnification×400.
Figure 23:
FIG. 23 is an image of a mouse skin section fixed with preparation A-Ia according to the present invention, and stained with AgNOR; magnification×1000 (oil).
Figure 24:
FIG. 24 is an image of a mouse skin section fixed with preparation A-Ia according to the present invention, and stained with AgNOR; magnification×1000 (oil).
Figure 25:
FIG. 25 is an image of a mouse skin section fixed with preparation A-Ia according to the present invention, and stained with AgNOR; magnification×1000 (oil).
Figure 26:
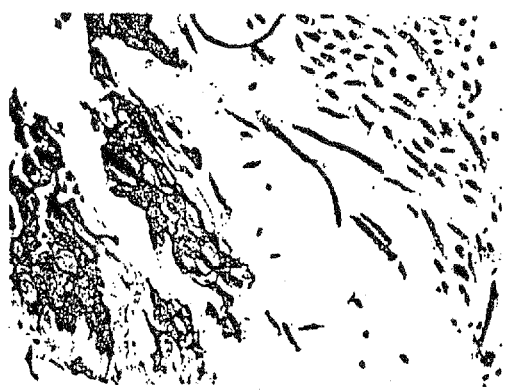
FIG. 26 is an image of a mouse skin section fixed with Solcoderm™ and stained with AgNOR; magnification×100.
Figure 27:
FIG. 27 is an image of a mouse skin section fixed with Solcoderm™ and stained with AgNOR; magnification×400.
Figure 28:
FIG. 28 is an image of a mouse skin section fixed with buffered formaldehyde 4% and stained with AgNOR; magnification×400.
Figure 29:
FIG. 29 is an image of a mouse skin section fixed with buffered formaldehyde 4% and stained with AgNOR; magnification×400.
Figure 34:
FIGS. 34a-b-Veruca vulgaris; 3 topical treatments; complete healing after 43 days.
Figure 34:
Figure 35:
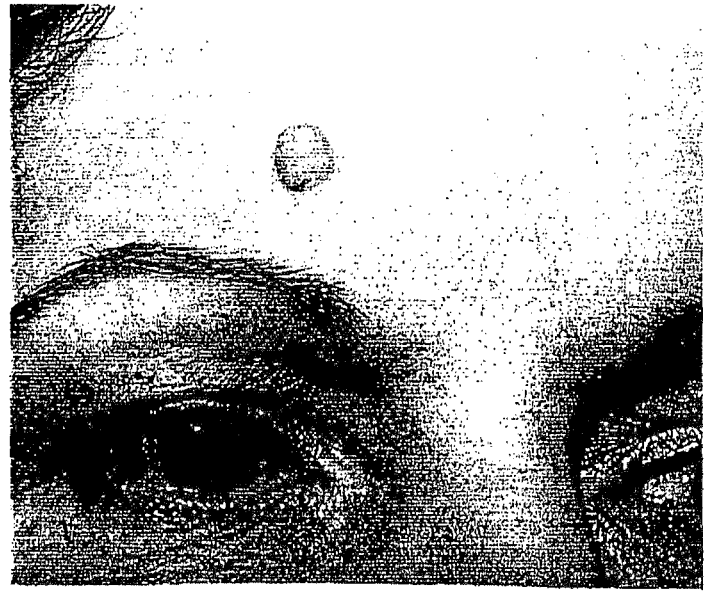
FIGS. 35a-b-Intradermal nevus; 1 topical treatment; scab dropped 18 days after treatment; pictures taken 39 days after treatment.
Figure 35:
Figure 39:
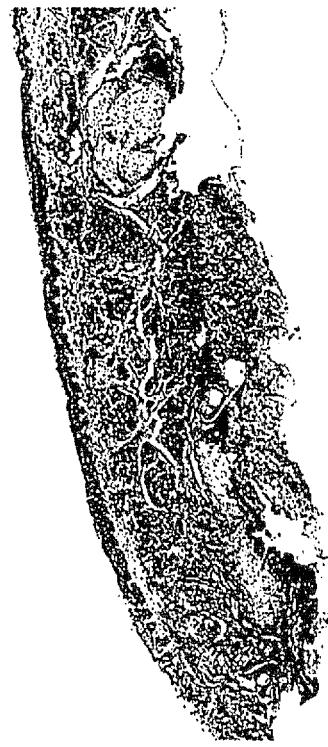
FIGS. 39-50 illustrate sections of a scab formed and detached following treatment of an intradermal nevus on the forehead of a 31 year old woman by a single topical application of one embodiment of the pharmaceutical preparation of the present invention.
Figure 40:
Figure 41:
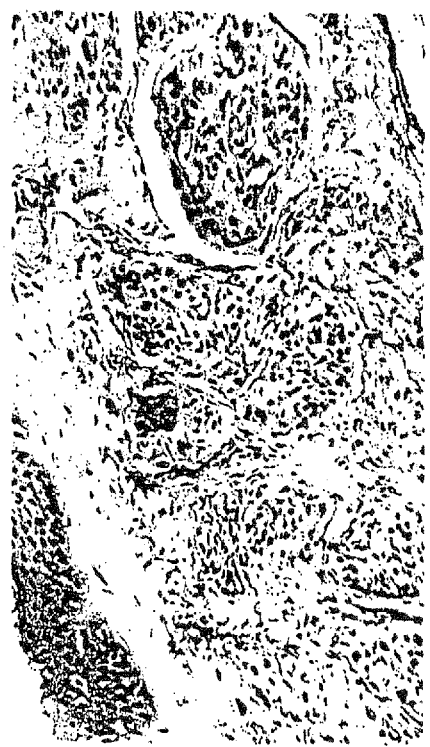
Figure 42:
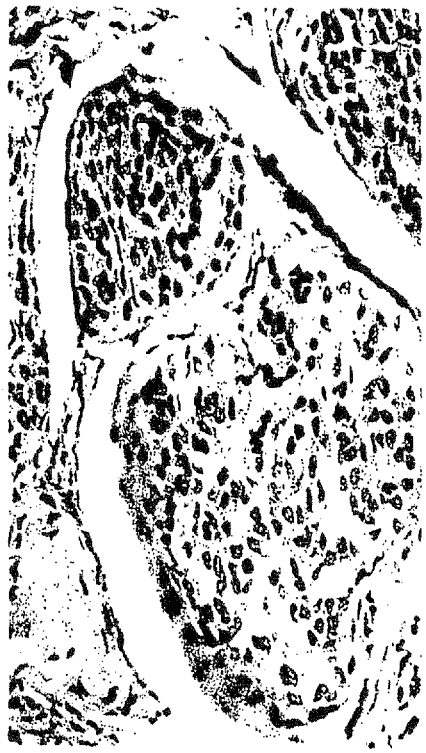
Figure 44:
Figure 46:
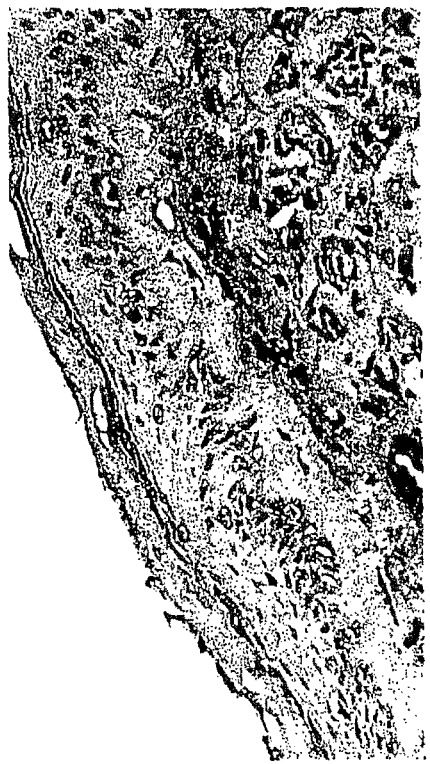
Figure 43:
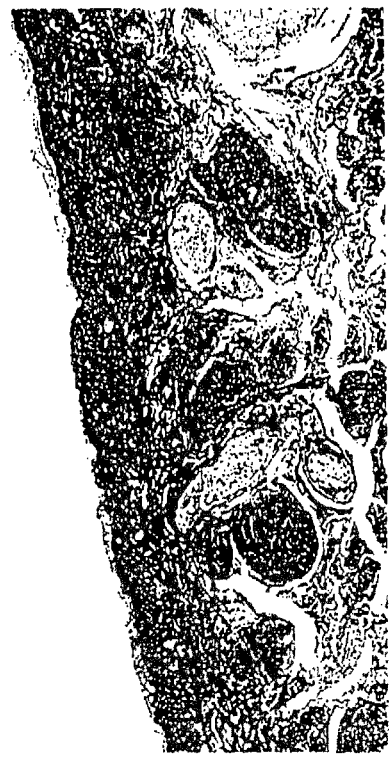
Figure 45:
Figure 48:
Figure 50:
Figure 47:
Figure 49:

As shown in FIGS. 1-29, tissue sections treated with preparation A-Ia and stained with H&E (FIGS. 1-3), Van-Gieson (FIGS. 10-13), or AgNOR (FIGS. 19-25), and tissue sections treated with preparation A-Ib and stained with H&E (FIGS. 4-5) or cytokeratin (FIG. 16) exhibited morphology which more closely resembles that of formaldehyde fixed controls (FIGS. 8, 9,15,18 and 28-29) as compared to tissue sections treated with Solcoderm" and stained with H&E (FIGS. 6-7), Van-Gieson (FIG. 14), cytokeratin (FIG. 17) or AgNOR (FIGS. 26-27).

As shown in FIGS. 19-29, the AgNOR stained tissue sections exhibited better than control morphology. Use of this stain enables clear visualization of the basal membrane, the epidermis-dermis border and nuclear matter, thus enabling quantification of NORs in every cell and determination of abnormal mitotic activity. This stain also enables evaluation of the proportion between nuclei and stroma as a parameter of proliferation of epithelial cells and as such is especially useful in the diagnosis of malignant melanoma.

Various parameters were taken into account during the design of the different versions of the preparation. If one considers the tissue penetration ability on the one hand and fixation quality on the other, versions a, b, a+ and b+ of Formulation A-I. (see Table 1) are particularly effective, where fixative treatment using version b enables faster softening of the tissue and is therefore more suitable for lesions and tumors with a harder consistency or those well protected by an especially thick layer of keratin.

In light of the data presented herein, it is evident that several versions of the pharmaceutical preparation of the present invention can be effectively used as a treatment/fixative preparation since it enables retrospective histopathological diagnosis of tissue treated thereby.

Following determination of its fixative properties preparation A-I was used in a series of clinical studies in order to determine its effectiveness in treating skin lesions (Example 2) as well as to determine the level of discomfort, if any, when used in treatment (Example 3).

Example 2

Clinical Study

A clinical study involving 87 patients, with a total number of 228 lesions was conducted. The patients were divided into 2 main groups: group A-highly responsive STLs; group B-less responsive STLs.

The diagnosed STLs of Group A included: Intradermal Nevus, Fibroepithelial Polyp, Dermatofibroma, Seborrheic Keratosis, Condyloma Acuminata and Veruca Plana. The diagnosed STLs of Group B included Veruca vulgaris and Haemangioma.

The patients were treated with preparation A-Ib described hereinabove in Table 1. Treatment regimen was as follows: an applicator was dipped into the preparation and used to wet the lesion. The entire area of the lesion was moistened, while avoiding contact between the preparation and surrounding healthy tissues. If the healthy tissue adjacent to the lesion was moistened, it was immediately wiped dry with a cotton swab.

Using moderate pressure on the applicator, both perpendicularly to the skin and at a 45° angle if the lesion protrudes

TABLE 2

Results of a clinical study

| Compound in ml. | | | | | Score | | | |
|---|---|---|---|---|---|---|---|---|
| TCA 90% (w/w) | Hcl 35% (w/w) Stock | FA 85% (w/w) Stock | Formaldehyde 40% | H$_2$O | H & E | Ag NOR | Cytokeratin | Average Score |
| 0.6 | | | | 0.4 | 1-2 | 3 | 2 | 2.16 |
| | 0.6 | | | 0.4 | 1 | 1 | 1 | 1.00 |
| | | 0.6 | | 0.4 | 2 | 3-4 | 2 | 2.50 |
| 0.3 | 0.3 | | | 0.4 | 1-2 | 3 | 2 | 2.16 |
| 0.3 | | 0.3 | | 0.4 | 1-2 | 4 | 2 | 2.50 |
| | 0.3 | 0.3 | | 0.4 | 1 | 1 | 1 | 1.00 |
| 0.2 | 0.2 | 0.2 | | 0.4 | 2-3 | 4 | 3 | 3.16 |
| 0.2 | 0.2 | 0.2 | 0.1 | 0.3 | 3 | 5** | 3 | 3.66 |
| Form A-I a (1.0 ml)* | | | | | 2-3 | | 3 | 3.16 |
| Form A-I b (1.0 ml)* | | | | | 3 | 5 | 2-3 | 3.5 |
| Form A-I a+ (1.0 ml)* | | | | | 3 | 5** | 3 | 3.66 |
| Form A-I b+ (1.0 ml)* | | | | | 3-4 | 5** | 2-3 | 3.66 |
| Solcoderm ™ (1.0 ml) | | | | | 1 | 1 | 1 | 1.00 |
| Solcoderm ™ new version 1996 (1.0 ml) | | | | | 1 | 1 | 1 | 1.00 |
| Control-buffered formaldehyde 4% (1.0 ml) | | | | | 4 | 4 | 4 | 4.00 |

*For compositions-see Table 1.
**Better than control.

above the skin, the preparation was forced into the treated tissue. As the liquid penetrated, the lesion softens, and the application treatment was stopped. The patient was instructed to moisten the treated area several times daily, using absorbent cotton saturated with 70% alcohol, beginning 24 hours after the treatment, and especially after showering.

Following this treatment regimen, the tissue undergoes fixation and gradual drying, until the lesion completely separates from its base tissue, and falls off. Since this separation does not occur until re-epithelialization ends, the exposed skin is dry, smooth, healthy, and manifests no signs of local infection, i.e., suppuration, bleeding, or festering. The slight hyperemia in the treated area gradually subsides.

The patient usually feels a local, tolerable, burning sensation, which does not require the use of local anesthesia, and which subsides completely several minutes following the end of the treatment. There is no need for local bandaging, as the scab in itself serves as a biological bandage. If the fixed lesion is to be sent for histopathological examination, the treated area is covered with a breathing micropore bandage, to prevent loss of the scab.

Results

Table 3 below summarizes the results of the clinical trial. Among the 87 patients treated, 11 did not appear for the follow-up examination carried out 6 months or more following treatment; these cases have not been included in the data presented here.

FIGS. 30a1-38c2 are Images of patients having skin lesions prior to (a1 and a2) and following (b1, b2, c1 and c2) treatment with the preparation of the present invention. STLs types treated in this study were divided into highly responsive STLs and less responsive STLs in order to obtain a more clear representation of the collected results, thus permitting precise evaluation of the data concerning the efficiency of the preparation of the present invention.

TABLE 3

Clinical trial results

| Group | Diagnosis | Number of STLs | Number of successful results | Failures | Number of local applications (Average) | Recurrences |
|---|---|---|---|---|---|---|
| A | Intradermal nevus | 62 | 62 | — | 1-2 (1.11) | — |
|   | Fibrocpithelial Polyp (skin tag) | 15 | 15 | — | 1-2 (1.13) | — |
|   | Dermatofibroma | 6 | 6 | — | 1-2 (1.33) | — |
|   | Seborrheic keratosis | 20 | 20 | — | 1-2 (1.30) | — |
|   | Condyloma | 19 | 19 | — | 1-2 (11.36) | 2 (10.5%) |
|   | Veruca plana | 12 | 12 | — | 1-2 (1.25) | — |
| B | Veruca vulgaris (common warf) | 57 | 53 | 4 | 1-4 | 6 |
|   | Haemangioma | 11 | 11 | — | 1-3 (1.90) | — |

*The treatment was considered a failure when a lesion of veruca vulgaris did not completely respond to 4 local applications.

The crust which formed at the treated region was detached in almost all cases 9-22 days following treatment (maximum 27 days). Hyperpigmentation developed In 3.4% of treated ~TLs, while hypopigmentation developed in 6.4% of the cases. Superficial scarring was noted for 2.9% of the treated STLs. In most cases, slight pigmentation changes, which usually appear after the crust drops, gradually vanished in within a few days.

Thus, the preparation of the present invention provides a suitable inexpensive and readily available alternative to destructive treatment methods to (e.g., laser and cryosurgery) while providing the physician with the ability to use the treated tissue for histopathological analysis if need be.

Example 3

Staining of Tissue Treated with the Pharmaceutical Preparation of the Present Invention Sections of a scab formed and detached following treatment of an intradermal nevus on the forehead of a 31 year old woman by a single topical application of preparation A-Ib were stained with Hematoxylin & eosin, VanGieson, Cytokeratin, HMB 45 and AgNOR. The results are shown in FIGS. 39-50.

Example 4

Comparison of the Degree of Burning Sensation Between the Composition of the Present Invention and Soloderm™

Treatments were conducted concurrently on 14 men and women with pairs of adjacent tumors that were more or less identical in size and nature in order to compare the burning sensation of the preparation of the present invention with that produced by Solcoderm™, a commercially available preparation. The patients were asked to answer two questions at the end of the treatment regimens, which treated side burn/hurt more (with an option to answer identical burning/pain) and if the one that burns more or is more painful is defined as a level 3 burn/pain, how would you define the other treated area, using the following scale:

Level 0: no sensation at all.
Level 1: slight sensitivity
Level 2: moderate sensitivity
Level 3: severe sensitivity Results As shown m Table 4 below, the preparation of the present invention caused, on an average, slight to moderate sensitivity, whereas Solcoderm™ caused severe sensitivity in most patients treated.

TABLE 4

| | Results of burning sensation assessment | | | | | | | | | | | | | | |
|---|---|---|---|---|---|---|---|---|---|---|---|---|---|---|---|
| | Patient No. | | | | | | | | | | | | | | Average |
| | 1 | 2 | 3 | 4 | 5 | 6 | 7 | 8 | 9 | 10 | 11 | 12 | 13 | 14 | Score |
| Solcoderm™ | 3 | 3 | 3 | 2, | ~ | 3 | 3 | 3 | 3 | 3 | 2 | 3 | 3 | 3 | 2.85 |
| Form. A-Ib | 2 | 1 | 2 | 3 | 1 | 3 | 3 | 1 | 1 | 1 | 3 | 1 | 1 | 2 | 1.78 |

Thus, treatment with the preparation of the present invention causes far less discomfort to the patient as compared to Solcoderm™.

Example 5

The Therapeutic Kit

Figure 52:
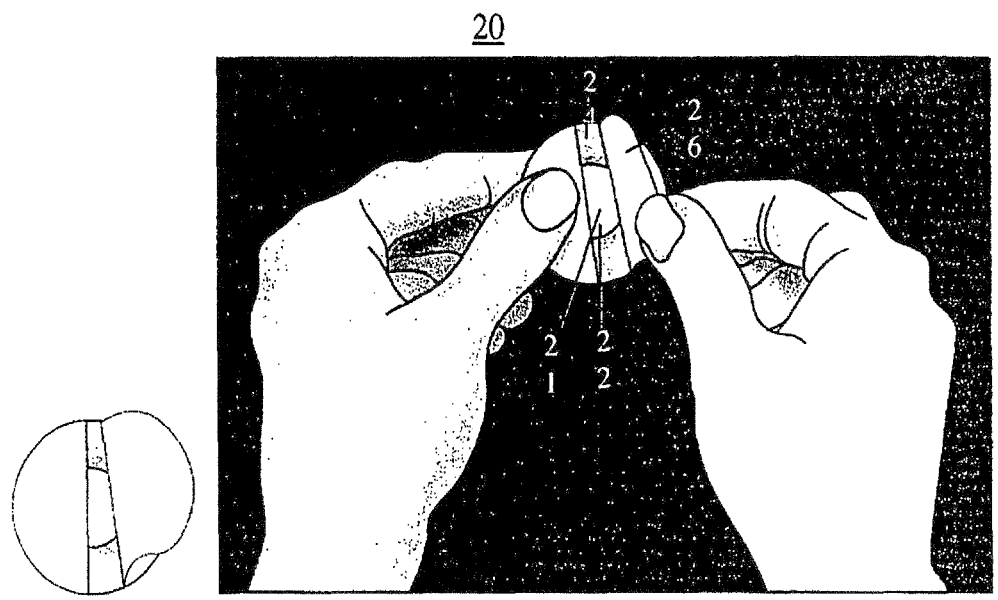
FIGS. 52a-b illustrate an adhesive bandage configured for treating skin lesions according to the teachings of the present invention.
Figure 52:
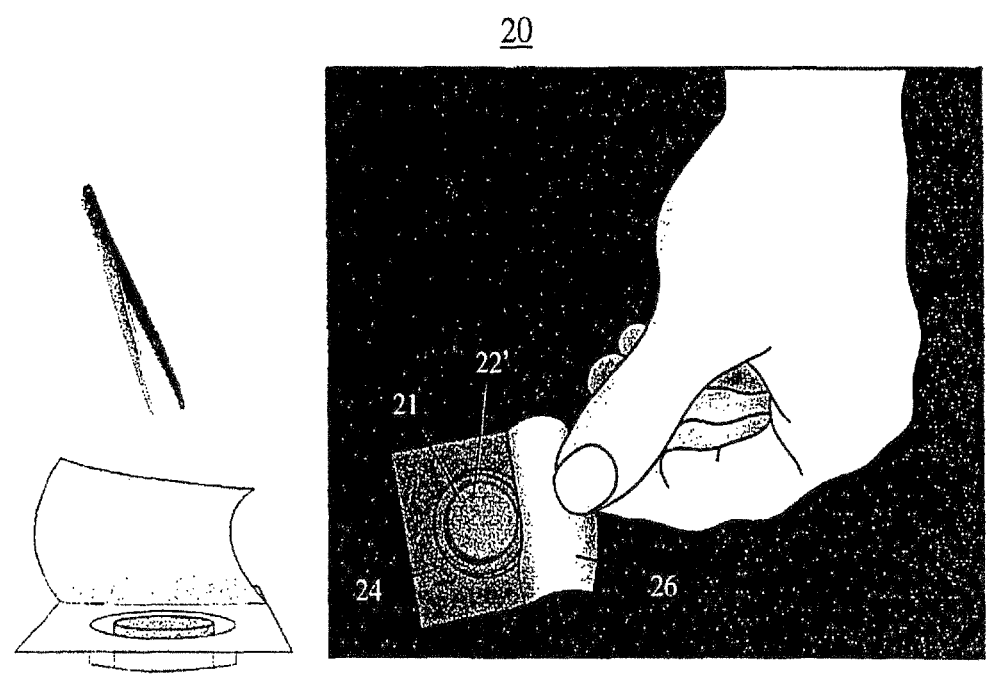

The compositions of the present invention may be applied using a therapeutic kit. Such a kit includes:
(i) an ampoule containing the medicine;
(ii) several specially adapted applicators of different diameters (described in detail below);
(iii) breathing micropore adhesive tape;
(iv) small paper envelope for sending the specimen, that is also a form for recording the patient's details, date, and name of attending physician.
(v) stand and handle for ampoule; and
Adhesive Bandage The preparation of the present invention can also be applied VIa an adhesive bandage. As specifically shown in FIGS. 52a-b, such a bandage 20 includes an applicator 21 (e.g., pad 22 or reservoir 22') which is soaked with or contains the pharmaceutical preparation of the present invention and an adhesive tape 24 which is attached to applicator 21. Adhesive tape 24 is configured for attaching to a skin region thereby positioning applicator 21 against a portion of the skin region which includes the skin lesion. Upon such positioning the pharmaceutical preparation of the present invention is applied to the skin lesion via diffusion or active release (e.g., physical pressure on applicator pad ruptures microvesicles which release the preparation or slow release from microcapsules). A removable (e.g., peelable) cover 26 protecting applicator 21 may also be employed.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, and patent applications mentioned in this specification are herein incorporated in their entirety by reference into the specification, to the same extent as if each individual publication, patent, or patent application was specifically and individually indicated to be incorporated herein by reference. In addition, citation or identification of any reference in this application shall not be construed as an admission that such reference is available as prior art to the present invention.

What is claimed is:

1. A pharmaceutical preparation for treating a skin or mucous membrane lesion consisting of trichloroacetic acid and formic acid, wherein the pharmaceutical preparation mummifies the skin or mucous membrane lesion such that the lesion is completely separated from a base tissue thereof and falls off.

2. A method of treating a skin or mucous membrane lesion comprising applying to the skin or mucous membrane lesion the pharmaceutical preparation of claim 1, wherein the pharmaceutical preparation mummifies the skin or mucous membrane lesion such that the lesion is completely separated form a base tissue thereof and falls off.

* * * * *